United States Patent
D'Amelia et al.

(10) Patent No.: US 6,511,679 B2
(45) Date of Patent: *Jan. 28, 2003

(54) BREATH FRESHENING COMESTIBLE PRODUCT AND METHOD OF CONTROLLING BREATH MALODOR

(75) Inventors: Ronald D'Amelia, Hicksville, NY (US); Joseph Bell, Bethlehem, PA (US); Walter Hopkins, Bridgewater, NJ (US); Saul Scheinbach, Bronx, NY (US); Jack Homcy, Paterson, NJ (US); Martin Cole, Cherrybroon (AU); Robert J. Huzinec, Hummelstown, PA (US); Judith K. Cooley, Hummelstown, PA (US); Thomas J. Carroll, Oak Ridge, NJ (US)

(73) Assignee: Hershey Chocolate and Confectionary Corporation, Wheat Ridge, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/923,095

(22) Filed: Aug. 6, 2001

(65) Prior Publication Data

US 2002/0076433 A1 Jun. 20, 2002

Related U.S. Application Data

(63) Continuation-in-part of application No. 09/395,322, filed on Sep. 13, 1999, now Pat. No. 6,280,769.

(51) Int. Cl.⁷ ............................ A61K 9/20; A61K 9/68; A23G 3/30; A23G 3/00

(52) U.S. Cl. .................... 424/464; 424/48; 424/465; 426/3; 426/660

(58) Field of Search .................... 424/48, 464, 465; 426/3, 660

(56) References Cited

U.S. PATENT DOCUMENTS

| | | | |
|---|---|---|---|
| 4,311,722 A | 1/1982 | Vink et al. | 426/660 |
| 4,673,577 A | 6/1987 | Patel | 426/5 |
| 4,724,151 A | 2/1988 | Mansukhani et al. | 426/3 |
| 5,154,939 A | * 10/1992 | Broderick et al. | 426/5 |
| 5,284,659 A | * 2/1994 | Cherukuri et al. | 424/441 |
| 5,286,501 A | 2/1994 | Song et al. | 426/3 |
| 5,342,631 A | 8/1994 | Yatka et al. | 426/3 |
| 5,456,932 A | * 10/1995 | Fuisz et al. | 426/548 |
| 6,030,605 A | 2/2000 | D'Amelia et al. | 424/48 |

* cited by examiner

Primary Examiner—Thurman K. Page
Assistant Examiner—S. Tran
(74) Attorney, Agent, or Firm—Scully, Scott, Murphy & Presser

(57) ABSTRACT

A comestible product which includes inulin, a second component and a divalent zinc or copper. When the comestible product is a tablet, a pressed tablet, a lozenge, a hard candy or a chewy candy, the second component is a formentable carbohydrate which may, optionally, include a polyol. When the comestible product is a chewing gum the second component is a polyol, a formentable carbohydrate or mixtures thereof. The comestible product is useful in controlling breath malodor.

14 Claims, No Drawings

BREATH FRESHENING COMESTIBLE PRODUCT AND METHOD OF CONTROLLING BREATH MALODOR

REFERENCE TO RELATED APPLICATION

This is a continuation-in-part of U.S. patent application Ser. No. 09/395,322, filed Sep. 13, 1999, now U.S. Pat. No. 6,280,769.

BACKGROUND OF THE DISCLOSURE

1. Field of the Invention

The present invention is directed to a comestible product which effectively controls breath malodor. More particularly, the present invention is directed to a breath malodor-controlling comestible product which includes inulin.

2. Background of the Prior Art

Bad breath, medically referred to as breath malodor, is primarily caused by volatile sulfur compounds (VSC), which are mainly hydrogen sulfide ($H_2S$) and methyl methyl mercaptan ($CH_3SH$). Although the identification of VSC as the cause of bad breath is well established in the art, recent research has rebutted a common misconception regarding the basis of generation of VSC. Many health professionals previously believed that breath malodor, caused by VSC, was the result of intestinal malfunction. However, recent medical and dental research has established that VSC-causing breath malodor is generated in the human oral cavity, i.e. the mouth, rather than in the intestine.

Specifically, Gram-negative bacteria in the oral cavity, which are anaerobic, e.g. *Porphyromonas denticola, Treponema gingivalis, Prevotella intermedia,* Fusobacterium and Bacteroides, metabolize protein to produce VSC. It is theorized that it is protein, present in saliva, that is the subject of anaerobic metabolism, which primarily occurs in the tongue dorsum.

This identification of the cause of breath malodor suggests methods of its control. Those skilled in the microbiological arts are aware that Gram-negative bacteria thrive under alkaline conditions but are inactive under acidic conditions. Thus, the generation of an acid environment in the mouth cavity, it is believed, would go a long way towards controlling this condition.

This theory has not been pursued in the past due to the well established association between the generation of acid in the oral cavity and the formation of tooth caries. Thus, the suggestion that sucrose-rich foods, such as candies, gums and the like, could be used to fundamentally control breath malodor has not, in the past, been considered a viable solution to breath malodor since the Gram-positive bacteria in the oral cavity that metabolize sucrose cause caries.

However, it is not the generation of acid which causes caries. Acid in and of itself is quickly removed from the enamel of teeth by saliva in the oral cavity since the acid generated by Gram-positive bacteria is soluble in saliva. The fundamental problem associated with acid production in the oral cavity, caused by metabolism of sucrose, lies in the production, by Gram-positive bacteria, of plaque which is deposited on the enamel of teeth. That plaque protects the acid from dissolution by saliva, since plaque is not soluble in saliva. Thus, the acid is fixed to the enamel of teeth with the resultant formation of acid-induced caries.

The above discussion presents a solution to this seeming dilemma. If a foodstuff could be found which is metabolized by Gram-positive bacteria, which generate acid and thus prevents Gram-negative bacteria from actively metabolizing protein, but which acid so generated is not insoluble in saliva, the problem of breath malodor could be solved without introducing the associated problem of enhancing the formation of caries.

Of course, if the formation of caries is not deemed critical, i.e., in cases where only small amounts of a comestible is to be ingested or where the comestible is ingested infrequently, then the problem of breath malodor can be even more effectively addressed by the inclusion of a sugar component.

Whether a sugar ingredient is present or not, inulin, a naturally-occurring class of fructooligosaccharide molecules, has long been known for its ability to resist human enzymes and reach the colon largely undigested where the inulin is broken down to short chain fatty acids by intestinal microflora.

It is understood that most intestinal microflora cannot metabolize inulin. However, the presence of inulin stimulates the growth of bacteria that do metabolize inulin, i.e. bifdobacteria and lactobacilli. It is for this reason that inulin is deemed a beneficial agent in the treatment of intestinal disorders.

There has been no suggestion in the medical or dental literature that inulin could have an impact in the prevention or alleviation of breath malodor. However, it is known that many streptococci, which are Gram-positive bacteria, present in the oral cavity, can metabolize inulin to produce acid. It is speculated that inulin can thus reduce breath malodor in the same manner as does sucrose. However, while inulin reduces pH in the oral cavity, as does sucrose, it is questioned whether inulin would stimulate the development of tooth caries.

Prior art pertinent to the above discussion includes U.S. Pat. No. 4,311,722. The '722 patent discloses a hard candy having excellent color and long shelf-life which contains 50% or more fructose. The hard candy may optionally include dextrin and inulin or cellulose gums. The dextrin and inulin of the fructose-containing hard candy glass during manufacture. The inulin constituent represents between 0 to about 20% of the hard candy. When included in the hard candy, the inulin is preferably present in an amount of about 1% to about 10% by weight, based on the total weight of the candy.

U.S. Pat. No. 5,286,501 is directed to a petroleum wax-free chewing gum having enhanced flavor release and breath freshening. The chewing gum of the '501 patent includes a petroleum wax-free gum base which contains at least 1 wt. % of at least one elastomer plasticizer and at least 0.01 wt. % of a flowing agent. An especially important requirement of the chewing gum of the '501 patent is that the gum base have an average weighted Solubility Parameter of from about 16 to 21 S.P.U.s and that at least 5 wt. % of the flavoring agent has a Solubility Parameter of from about 0.5 S.P.U. greater than, or less than, the weight Solubility Parameter of the gum base. The chewing gum of the '501 patent preferably includes binders and bulking agents. When present these agents may be corn syrups, inert sugar syrups, hydrogenated starch hydrolysates, sucrose syrups and oligosaccharides.

U.S. Pat. No. 5,342,631 relates to another petroleum wax-free chewing gum. This gum contains a binder containing at least 35 weight percent of at least one poorly metabolized oligosaccharide having noncariogenic characteristics. The average degree of polymerization ranges from at least 3 to about 50 although the degree of polymerization may be as high as 100.

BRIEF SUMMARY OF THE INVENTION

It has now been discovered that an inulin-containing comestible significantly controls breath malodor with or without the inclusion of a sugar ingredient.

In accordance with the present invention a comestible product selected from the group consisting of a tablet, a pressed tablet, a lozenge, a hard candy and a chewy candy is provided which comprises between about 40% and about 95% inulin, between about 5% and about 60% formentable carbohydrate and between about 0.02% and about 0.3% divalent zinc or copper compound, said percentages being by weight, based on the total weight of the comestible product.

In further accordance with the present invention a chewing gum is presented which includes between about 40% and about 95% inulin, between about 5% and about 60% of a second component selected from the group consisting of a polyol, a formentable carbohydrate and mixtures thereof, between about 0.02% and about 0.3% divalent zinc or copper compound and between about 5% and about 50% gum base, said percentages being by weight, based on the total weight of the chewing gum.

In further accordance with the present invention, a method of controlling breath malodor is set forth. This method comprises ingesting or chewing a breath malodor controlling effective amount of a comestible product which includes between about 40% and about 95% inulin, between about 5% and about 60% polyol and/or formentable carbohydrate and between about 0.02% and about 0.3% divalent zinc or copper compound, said percentages being by weight, based on the total weight of the comestible product.

DETAILED DESCRIPTION

Inulin is a linear oligomer comprising β-D-fructose linked to a terminal α-D-glucose. Inulin is thus a non-reducing sugar having the structural formula $GFr_n$, where G is α-D-glucose; Fr is β-D-fructose; and n is an integer of 2 to 60. Because the formula for inulin emphasizes that it is substantially all fructose, inulin is often referred to as "fructan."

The comestible product of the present invention includes a substantial concentration of inulin. In a preferred embodiment the inulin component of the comestible product comprises between about 40 weight % and about 95 weight %. More preferably, the inulin concentration is the range of between about 45 weight % and 85 weight %. Still more preferably, the concentration of inulin is the range of between about 50 weight % and about 75 weight %. Most preferably, the inulin of the comestible product of the present invention represents between about 50 weight % and about 60 weight %, based on the total weight of the comestible product.

A second component of the comestible product of the present application is a polyol. A polyol is a water soluble polyhydric alcohol. Preferred polyols useful in the comestible product of the present invention include mannitol, xylitol, isomalt, sorbitol, lactitol, maltitol, erythritol, maltitol syrup, hydrogenated starch hydrolysate, hydrogenated glucose, hydrogenated glucose syrup, hydrogenated disaccharides, hydrogenated polysaccharides and mixtures thereof.

Of the polyols within the contemplation of the present invention sorbitol, maltitol and mannitol are preferred. Of these polyols, sorbitol is most preferred.

The polyol constituent of the comestible product of the present invention represents between about 5 weight % and about 60 weight %, based on the total weight of the comestible product. More preferably, the concentration of the polyol is in the range of between about 15 weight % and about 55 weight %. Still more preferably, the polyol constituent is present in an amount of between about 25 weight % and about 50 weight %. Most preferably, the polyol constituent comprises between about 40 weight % and about 50 weight %, based on the total weight of the comestible product.

As an alternative to a polyol as the second component of the comestible product of the present invention, the polyol, which is a non-fermentable carbohydrate, may be replaced with a fermentable carbohydrate. A fermentable carbohydrate is a scientific term for what the lay person would express as sugar. Fermentable carbohydrates within the contemplation of the present invention include sucrose, glucose, dextrose, maltose, lactose, dextrin, invert sugar, fructose, galactose, corn syrup solids, maltodextrins, starch, starch derivatives, mixtures thereof and the like. Of these, sucrose and dextrose are particularly preferred. Most preferably, the fermentable carbohydrate is sucrose.

Yet another embodiment of the comestible of the invention encompass a second component which includes at least one polyol (non-fermentable carbohydrate) and at least one formentable carbohydrate.

A third essential component of the comestible product of the present invention is a physiologically acceptable divalent zinc or copper compound. In view of the requirement that the zinc or copper compound be physiologically acceptable and in further view of the necessity of not including a zinc or copper compound whose taste is unacceptably bitter, preferred divalent zinc or copper compounds employed in the comestible product are organic compounds. As such, preferred divalent zinc or copper compounds utilized in the comestible product of the present invention include zinc gluconate, zinc lactate, zinc stearate, zinc tartrate, zinc succinate, copper gluconate, copper lactate, copper stearate, copper tartrate and copper succinate. Although a single divalent zinc or copper compound is contemplated for inclusion in the comestible product of the present invention, the utilization of two or more divalent zinc or copper compounds may be utilized.

Of the zinc or copper compounds preferred for use in the comestible product zinc gluconate, zinc lactate, copper gluconate and copper lactate are more preferred. Of these compounds, zinc gluconate and zinc lactate are still more preferred. The most preferred divalent zinc or copper compound is zinc gluconate.

The inclusion of a divalent zinc or copper compound synergistically aids in the control of breath malodor. That is, the presence of a divalent zinc or copper compound in the comestible product of the present invention has been found to reduce VSC to a greater degree than the utilization of a comestible product which, although including the other essential components of the comestible product of the present invention, does not include a divalent zinc or copper compound.

The concentration of the divalent zinc or copper compound in the comestible product of the present invention is in the range of between about 0.02 weight % and about 0.3 weight %, based on the total weight of the comestible product. More preferably, the divalent zinc or copper compound is present in a concentration in the range of between about 0.05 weight % and about 0.2 weight %.

Additional components that may be preferably included in the comestible product of the present invention include flavorants and colorants. Although flavorants and colorants are contemplated for use in all forms of the comestible product of the present invention, additional components may be present therein depending upon the form of the comestible product.

Suitable flavorants of the comestible product may be natural or artificial flavors. Examples of flavorants preferred for use in the comestible product include peppermint oil, menthol, spearmint oil, vanilla, cinnamon, wintergreen oil, which is methyl salicylate, fruit flavorings including but not limited to lemon oil, orange oil, grape flavor, lemon oil, grapefruit oil, apple, apricot essence and combinations thereof. The concentration of flavorant is a function of the particular flavor and may be present in the range of between about 0.5 weight % and about 3 weight %.

Other preferred components of the comestible product include pigments, such as titanium dioxide, and food colorants, such as beta carotene, betanin, turmeric and other USFDA-approved dyes suitable for food applications.

The comestible product of the present invention is preferably provided in the form of tablets, lozenges, hard candies, chewy candies, pressed tablets and chewing gums. It is emphasized that pressed tablets are more commonly referred to as pressed mints because of the flavor usually associated with such products. However, the term pressed tablets represents a better designation since the flavorant of a pressed mint need not be mint. It is emphasized that this list of comestibles is incomplete. Other comestibles which may be formed from the components discussed above are within the contemplation of the present invention.

As stated above, other components of the comestible product are present as a function of the type of comestible product employed. For example, tablets, lozenges, pressed tablets and the like, particularly preferred classes of comestibles within the contemplation of the present invention, include a tableting lubricant. The tableting lubricant or, as it is also referred to, a binding agent, is present in the concentration of between about 0.1% and about 5% by weight. More preferably, the tableting lubricant is present in a concentration of between about 0.2 weight % and about 2 weight %. These concentrations are based on the total weight of the comestible product.

Tableting lubricants preferred for use in the comestible product include vegetable oils, such as coconut oil and soybean oil, medium chain triglycerides, magnesium stearate, aluminum stearate, calcium stearate, talc, starch, Carbowax and surfactants such as poloxamers. Of these tableting lubricants, magnesium stearate is particularly preferred.

In the event that the comestible product is in the form of a lozenge or a pressed tablet, a barrier agent is usually present, preferably in a concentration of up to about 2 weight %. The barrier agent provides a shiny surface as opposed to a tablet which, although having a smooth finish, is usually not shiny. In a preferred embodiment, the barrier agent is a hydrocolloid.

In the preferred embodiment wherein a lozenge, a tablet or a pressed tablet is utilized, these comestibles may be coated with a coating material. Among the coating materials suitable for use in this application are waxes, shellacs, carboxymethyl cellulose, ethylene-maleic anhydride copolymers and carragennan. A coating material is used to increase the time it takes for the tablet or lozenge to dissolve in the mouth. A coated tablet or lozenge is slow dissolving, providing sustained release of the active ingredients over a longer period of time, e.g. 3 to 5 minutes.

Another preferred form of the comestible product of the present invention is in the form of a chewing gum. A comestible product in the form of a chewing gum includes the basic ingredients discussed above, i.e. inulin, polyol and divalent zinc or copper compound, in combination with a gum base. In general, the gum base is present in an amount in the range of between about 5 weight % and about 50 weight % of the total chewing gum composition. More preferably, the gum base constituent is in the range of between about 10 weight % and about 30 weight %, based on the total weight of the chewing gum composition.

The gum base may be any water insoluble product commonly employed for this purpose. Illustrative examples of preferable insoluble products utilizable as the gum base of the present invention include natural and synthetic elastomers or rubbers and such biodegradable polymers as polycaprolactone, polylactic acid, polyhydroxyalkonates, copolymers of caprolactone, copolymers of lactic acid and copolymers of hydroxyalkonates. Of these, natural or synthetic rubbers or elastomers are preferred.

Among the natural rubbers are natural rubber, chicle, jelutong, gutta percha and crown gum. Other natural components of gum bases include resins, such as comarone resin, pontianak resin, copal gum, kauri gum, dammar gum, sweet bay gum, spruce gum and balsams. Synthetic elastomers and rubbers that may be utilized as the gum base include butadiene-styrene copolymers, isobutylene-isopropene copolymers, polyethylene, polyisobutylene, polyvinyl acetate, copolymers of vinyl acetate and mixtures thereof.

The gum base composition may additionally contain elastomeric solvents which aid in softening the elastomeric component. Such elastomeric solvents may include methyl, glycerol or pentaerythritol esters of rosins or modified rosins, such as hydrogenated, dimerized or polymerized rosins and mixtures thereof. Specific examples of preferred esters employed as solvents include the pentaerythritol ester of partially hydrogenated wood rosin, the pentaerythritol ester of wood rosin, the glycerol ester of partially dimerized rosin, the glycerol ester of polymerized rosin, the glycerol ester of tall oil resin, the glycerol ester of wood rosin and partially hydrogenated wood rosins and the partially hydrogenated methyl ester of rosin, such as polymers of α-pinene or β-pinene, terpene resins, including polyturpene and mixtures thereof.

The gum base may also include a variety of ingredients such as plasticizers or softeners. Preferred plasticizers and softeners include lanolin, stearic acid, sodium stearate, potassium stearate, glyceryl triacetate, propylene glycol, glycerol, acetylated monoglyceride, glyceryl diacetate, lecithin, fatty acids, glycerine and the like.

The gum base may further include waxes such as natural waxes, petroleum waxes, such as paraffin waxes, and microcrystalline waxes. The wax gum base additive is provided to obtain a variety of desired texture and consistency.

These additional materials are generally employed in amounts of up to about 50%, preferably between about 3% and about 30%, said percentages being by weight, based on the total weight of the gum base.

The chewing gum composition may additionally include conventional additives, such as emulsifiers, e.g. lecithin and glyceryl monostearate, fillers, such as dicalcium phosphate, tricalcium phosphate, aluminum hydroxide, magnesium hydroxide, alumina, aluminum silicates, calcium carbonate, talc and combinations thereof. Fillers are typically present in a concentration of between about 4% and about 30%, based on the total weight of the chewing gum.

The following example is given to illustrate the scope and spirit of the present invention. Because this example is given for illustrative purposes only, the scope of the present invention should not be deemed limited thereto.

EXAMPLE

Subjects were tested to determine the effect of comestible products, within the scope of the present invention, on breath malodor. Each of the subjects who took the test did not eat or drink for a period of 12 hours before testing. This refraining from eating and drinking was accompanied by a similar refraining from normal oral hygiene, such as tooth brushing, mouthwash rinsing and the like Upon testing, the subjects held their mouth closed while breathing through their noses to allow equilibration of mouth air for one minute. During this period the subjects did not swallow.

After one minute each subject inserted a sample tube through tightly closed lips into the mouth to a depth of 2 inches. The shoulder of the mouthpiece marked a limit of insertion. The end of the tube was placed toward the back of the mouth over the center of the tongue. During sample withdrawal, which took about 5 seconds, the subject stopped breathing. A 20 milliliter sample of mouth air was drawn to fill a 10 ml gas chromograph sample using a 60 ml disposable syringe. The sample tube was then removed from the mouth and the sample was injected into a gas chromagraph using a switching valve and the sample was thereupon analyzed.

A Hewlett Packard 7 5890 gas chromagraph was utilized in this test. The injector was equipped with a 10 port Valco circular sampling valve and a 25'×⅛" O.D×1/16" I.D. tube having a volume of 10 ml. The chromatographic column was 25'×⅛" Teflon packed with 5% polyphenyl ether (5 ring) and 0.5% phosphoric acid on 40–60 mesh Chromasorb-T. The chromatograph was characterized by all tubing, valves and connections in contact with the samples being Teflon-coated since glass or metal tend to absorb sulfur-containing compounds.

The gas chromatograph utilized a Flame Photometric Detector. Dry compressed air was used as the carrier gas to eliminate any solvent front peak from the chromatogram. Carrier gas flow was maintained at 15.3 ml/min.

The subjects were initially tested to determine their breath VSC concentration. They were thereupon provided with conventional 1.8 g pressed tablets within and outside the scope of the present invention. In ingesting the pressed tablets the subjects allowed the tablet to slowly dissolve in the their mouths over a period of about 3 to 5 minutes. The VSC concentration, i.e. hydrogen sulfide and methyl mercaptan, in the subjects=breath was thereupon immediately redetermined.

The test results are summarized below in the Table wherein 10 different constituency pressed tablet samples within and outside the scope of the present invention were tested. The result, the change in VSC in the breath of the subject after ingesting the pressed tablets, is reported along with the constituency of the tablets.

TABLE

| | Pressed Tablet Constituency, % by weight | | | Results, % Reduction in VSC | |
|---|---|---|---|---|---|
| Ex. No. | Sorbitol | Inulin | With 0.05% Zn Gluconate | $H_2S$ | $CH_3SH$ |
| CE 1 | 100 | 0 | No | 0 | 0 |
| CE 2 | 100 | 0 | Yes | 36 | 50 |
| CE 3 | 75 | 25 | No | 34 | 98 |
| CE 4 | 75 | 25 | Yes | 66 | 90 |
| CE 5 | 50 | 50 | No | 65 | 56 |
| 1 | 50 | 50 | Yes | 99 | 98 |
| CE 6 | 25 | 75 | No | 66 | 96 |
| 2 | 25 | 75 | Yes | 99 | 64 |
| CE 7 | 0 | 100 | No | 79 | 93 |
| CE 8 | 0 | 100 | Yes | 60 | 98 |

The above embodiments and examples are given to illustrate the scope and spirit of the present invention. These embodiments and examples will make apparent, to those skilled in the art, other embodiments and examples. These other embodiments and examples are within the contemplation of the present invention. Therefore, the present invention should be limited only by the appended claims.

What is claimed is:

1. A comestible product which comprises a product selected from the group consisting of a tablet, a pressed tablet, a lozenge, a hard candy and a chewy candy which includes between about 40% and about 95% inulin, between about 5% and about 60% fermentable carbohydrate selected from the group consisting of sucrose, glucose, dextrose, maltose, lactose, dextrin, invert sugar, fructose, galactose, com syrup solids, maltodextrins, starch, starch derivatives and mixtures therof and between about 0.02% and about 0.3% divalent zinc or copper compound, said percentage being by weight, based on the total weight of the product.

2. A comestible product in accordance with claim 1 wherein said inulin is present in a concentration in the range of between about 45% and about 85%; said fermentable carbohydrate is present in a concentration in the range of between about 15% and about 55%; and said divalent zinc or copper compound is present in a concentration in the range of between about 0.05% and about 0.2%.

3. A comestible product in accordance with claim 2 wherein said inulin is present in a concentration in the range of between about 50% and about 75%; and said polyol is present in a concentration in the range between about 25% and about 50%.

4. A comestible product in accordance with claim 3 wherein said inulin is present in a concentration in the range of between about 50% and about 60%; and said polyol is present in the concentration in the range between about 40% and about 50%.

5. A comestible product in accordance with claim 1 wherein said comestible product is a pressed tablet.

6. A comestible product in accordance with claim 1 wherein said fermentable carbohydrate is selected from the group consisting of sucrose and dextrose.

7. A comestible product in accordance with claim 6 wherein said fermentable carbohydrate is sucrose.

8. A comestible product in accordance with claim 1 including a tableting lubricant and binding agent, said lubricant and binding agent present in a concentration in the range of between about 0.1% and about 5%, said percentages being by weight, based on the total weight of the tablet.

9. A comestible product in accordance with claim 8 wherein said lubricant and binding agent is selected from the group consisting of a vegetable oil, medium chain triglycerides, magnesium stearate, aluminum stearate, calcium stearate, starch, Carbowax and poloxamer.

10. A comestible product in accordance with claim 9 wherein said lubricant and binding agent is magnesium stearate, said magnesium stearate present in a concentration in the range of between about 0.2% and about 2%.

11. A comestible product in accordance with claim 1 wherein said zinc or copper divalent compound is zinc gluconate or zinc lactate.

12. A comestible product in accordance with claim 11 wherein said divalent zinc or copper compound is zinc gluconate.

13. A comestible product which comprises a product selected from the group consisting of a tablet, a pressed tablet, a lozenge, a hard candy and a chewy candy which includes between about 40% and about 95% inulin, between about 5% and about 60% of at least one polyol and at least one fermentable carbohydrate wherein said polyol is selected from the group consisting of mannitol, xylitol, isomalt, maltitol, erythritol, maltitol syrup, hydrogenated starch hydrolysate, hydrogenated glucose, hydrogenated glucose syrup, hydrogenated disaccharides and hydrogenated polysaccharide, and said fermentable carbohydrate is selected from the group consisting of sucrose, glucose, dextrose, lactose, dextrin, invert sugar, fructose, levulose, galactose, corn syrup solids, maltodextrins, starch and starch derivatives, and between about 0.02% and about 3% divalent zinc or copper compound, said percentages being by weight, based on the total weight of the product.

14. A method of controlling both malodor comprising ingesting a breath malodor controlling effective amount of a comestible product which is selected from a group consisting of a tablet, a pressed tablet, lozenge, a hard candy and a chewy candy, said comestible product comprising between about 40% and about 95% inulin; between about 5% and about 60% of a second component selected from the group consisting of a polyol, a fermentable carbohydrate and mixtures thereof; wherein said polyol is selected from the group consisting of mannitol, xylitol, isomalt, maltitol, erythritol, maltitol syrup, hydrogenated starch hydrolysate, hydrogenated glucose, hydrogenated glucose syrup, hydrogenated disaccharides and hydrogenated polysaccharide, and said fermentable carbohydrate is selected from the group consisting of sucrose, glucose, dextrose, lactose, dextrin, invert sugar, fructose, levulose, galactose, corn syrup solids, maltodextrins, starch and starch derivatives, and between about 0.02% and about 0.3% divalent zinc or copper compound, said percentages being by weight, based on the total weight of the comestible product.

* * * * *